United States Patent
Leonhardt et al.

(10) Patent No.: US 11,872,731 B2
(45) Date of Patent: Jan. 16, 2024

(54) METHOD FOR PRODUCING A BEAM GUIDE GRID AND A BEAM GUIDE GRID PRODUCED IN ACCORDANCE WITH THE METHOD

(71) Applicant: LEONHARDT E.K., Hochdorf (DE)

(72) Inventors: Wolfgang Leonhardt, Hochdorf (DE); Gunnar Schmorl, Goppingen (DE)

(73) Assignee: LEONHARDT E.K., Hochdorf (DE)

( * ) Notice: Subject to any disclaimer, the term of this patent is extended or adjusted under 35 U.S.C. 154(b) by 732 days.

(21) Appl. No.: 16/977,953

(22) PCT Filed: Mar. 22, 2019

(86) PCT No.: PCT/EP2019/057253
§ 371 (c)(1),
(2) Date: Sep. 3, 2020

(87) PCT Pub. No.: WO2019/192859
PCT Pub. Date: Oct. 10, 2019

(65) Prior Publication Data
US 2021/0078219 A1  Mar. 18, 2021

(30) Foreign Application Priority Data
Apr. 4, 2018 (DE) ............... 10 2018 107 969.9

(51) Int. Cl.
| | |
|---|---|
| *B29C 45/00* | (2006.01) |
| *B29C 45/36* | (2006.01) |
| *G21K 1/02* | (2006.01) |
| *B29K 71/00* | (2006.01) |
| *B29K 103/06* | (2006.01) |
| *B29L 11/00* | (2006.01) |

(52) U.S. Cl.
CPC .......... *B29C 45/0013* (2013.01); *B29C 45/36* (2013.01); *G21K 1/02* (2013.01); *B29C 2045/363* (2013.01); *B29C 2045/366* (2013.01); *B29K 2071/00* (2013.01); *B29K 2103/06* (2013.01); *B29L 2011/00* (2013.01)

(58) Field of Classification Search
None
See application file for complete search history.

(56) References Cited

U.S. PATENT DOCUMENTS

| | | | |
|---|---|---|---|
| 6,470,072 B1 * | 10/2002 | Johnson | G21K 1/025 378/150 |
| 2006/0055087 A1 * | 3/2006 | Freund | G21K 1/025 264/328.18 |

FOREIGN PATENT DOCUMENTS

JP  2003-251658  *  9/2003 ............. B29C 45/26

* cited by examiner

*Primary Examiner* — Edwin C Gunberg
(74) *Attorney, Agent, or Firm* — McNees Wallace & Nurick LLC

(57) ABSTRACT

The invention relates to a process for producing a beam guiding grid (4), comprising a molding having a grid of passageways (40) and wall areas surrounding them, from radiation-absorbing metal powder and binder, especially tungsten powder and binder. Advantageous production is achieved in that the molding is produced by injection molding, wherein the homogenized mixture, as a prepared flowable injection compound, is injected using an injection molding machine into a molding tool (7) that produces the molding, into which movable mold cores (72) were introduced prior to filing with the molding composition.

12 Claims, 2 Drawing Sheets

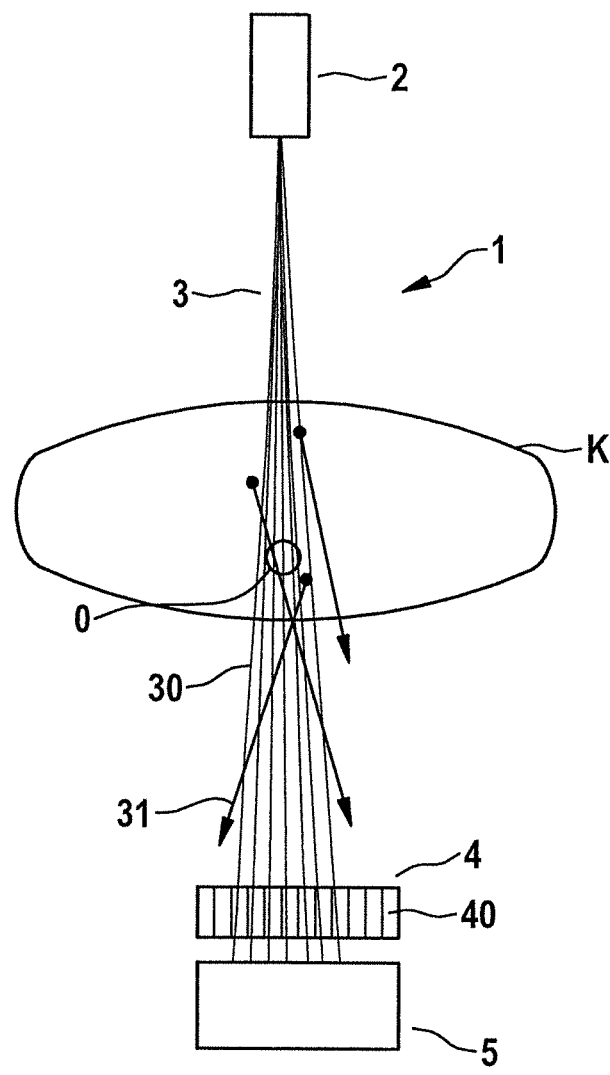
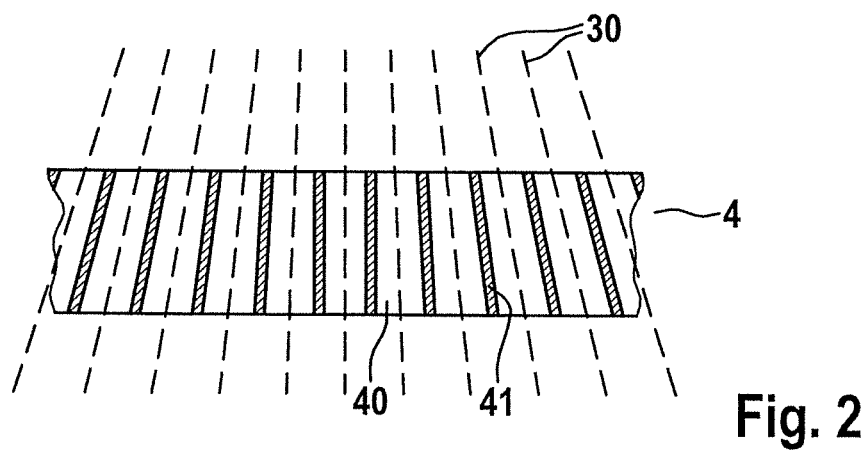
Fig. 1
Fig. 2

METHOD FOR PRODUCING A BEAM GUIDE GRID AND A BEAM GUIDE GRID PRODUCED IN ACCORDANCE WITH THE METHOD

FIELD OF THE INVENTION

The invention relates to a process for producing a beam guiding grid produced from a molding provided with a grid made of passageways and wall regions surrounding these, made of a mixture of radiation-absorbing metal powders and binders, especially tungsten powder and binders, and a beam guiding grid produced using this method.

BACKGROUND OF THE INVENTION

Beam guiding grids of this type, also known as anti-scatter grids or collimators, are used especially in X-ray or gamma-ray diagnostics, for example in computed tomography systems, to absorb as much as possible of the interfering scattered radiation, which is superimposed on the primary imaging rays in the imaging of an object to be investigated, and achieve the most interference-free imaging possible on a subsequent detector arrangement and obtain the most accurately readable image. Light guiding grids of this type have passageways surrounded by thin wall areas, for example in the thickness range of 100 μm and having an opening width of approximately 1 mm or less, the central passage axes of which are directed toward a mutual focal point in which the radiation source is disposed. This results in an oblique orientation of the individual passage channels relative to one another, with ensuing problems in the manufacturing of such beam guiding grids. The wall regions are made of a material that is as absorbent as possible and contains, for example, tungsten or a metal with a comparable absorption capacity for the X-rays or gamma radiation.

SUMMARY OF THE INVENTION

A process of the initially mentioned type for producing a beam guiding grid is proposed in EP 1 298 678 2. In this known process, a base body corresponding to the passage channels or the impermeable wall areas is built up using a rapid prototyping technique by layered solidification of a construction material through the action of radiation, and the beam guiding grid or anti-scatter grid or collimator is produced on this base body. For example, the material for absorbing the scattered radiation, in the liquid state, is filled into the interstices of the base body and solidified by cooling. The material of the base body can then be removed, so that only the framework of the absorbent material remains as the beam guiding grid. In another approach, the base body is formed in a negative mold, for example by filling or casting in nickel, and then a beam guiding grid can be produced from this negative mold in the above-described way. These examples show that high costs are required for producing a beam guiding grid.

In U.S. Pat. No. 6,470,072 B1 it is suggested that a beam guiding grid adjustable to various focal lengths be prepared by making it flexible. Injection molding is suggested for the production, and a mixture of powdered tungsten and thermoplastic material is mentioned. No more specific information is given on the production details, especially on how to overcome the aforementioned difficulties.

JP 2003-251 658 A shows the production of a fine-pore light guiding grid by injection molding, wherein a mold with movable partial molds penetrated by a group of parallel pins is used. However, a focusing grid is not obtained with such a device.

In US 2012/0085942 A1 a process for producing or collimators is disclosed, in which partial bodies made of tungsten powder are produced by sintering and assembled to make the collimators.

In US 2010/0276829 A1 the production of, among other things, beam guiding grids with a high aspect ratio by molding a molding composition containing, for example, 80 wt.-% to 98 wt.-% powdered material, such as tungsten powder, and binder in a mold is illustrated.

DE 10 2011 050 963 A1 shows a process for producing an anti-scatter X-ray grid in which a substrate with channels is prepared and then coated on the side walls with a material that does not absorb X-rays, and on top of this, with a material that absorbs das X-rays. Processes for producing the substrate, listed without further details, are injection molding, lasing, mechanical working, plasma etching and the like, and mentions as the substrate material, which is also non-absorbent for X-rays, thermoplastics, PEEK, graphite, aluminum and combinations thereof. The axial alignment of the channels may correspond to the cone of X-rays emerging form the source.

US 2013/0193329 A1 shows a neutron scintillator composition consisting of a neutron scintillator and a binder. In U.S. Pat. No. 5,034,157, a mixture suitable for injection molding, containing a polyether ketone matrix material such as PEEK resin is disclosed.

In U.S. Pat. No. 7,839,981 B2, a beam guiding grid made of various materials and a corresponding production process are shown.

The present invention addresses the problem of specifying a process for producing a beam guiding grid of the above-described type, with which in particular large numbers of parts can be produced as economically as possible. In addition, such economically produced beam guiding grid and the use thereof are to be provided.

This problem will be solved in terms of the process by the procedure specified in claim 1. For the beam guiding grid, the problem will be solved with the features stated in claim 8. With regard to the system and its application, the problem will be solved with the features of claims 12 and 13 respectively.

Thus regarding the process it is provided, in connection with the features of the main claim, that the molded body be produced by injection molding, wherein the homogenized mixture is packed as an injection mass, prepared in flowable form, into a molding tool that produces the molded body, into which the mold core, movable before introduction of the injection mass, is introduced.

Using these measures, which may also relate to a compression injection molding process within the scope of injection molding, using an appropriately designed mold, economical manufacturing of particularly high numbers of pieces will be achieved. With this, premium-grade beam guiding grids can be produced with consistently high quality, and in particular, largely problem-free inner wall surfaces in the wall areas can be obtained.

Corresponding benefits are also obtained for the beam guiding grid obtained in this way and the system and/or application based thereon.

Various embodiments of the process consist of the fact that a thermoplastic material or a duroplastic material preheated and plasticized for the injection process is used as the binder.

An advantageous additional measure for the production and the quality of the beam guiding grid obtained consists of the fact that the thermoplastic material used is a polyether ketone, especially polyether ether ketone (PEEK).

Additional advantageous measures for the performance of the process and the function of the beam guiding grid include the fact that the ratio of metal powder, especially tungsten powder, to binder is in the range of 30/70 to 98/2 percent by volume. For example, ranges of 40/60 to 95/5, of 50/50 to 90/10, especially 60/40 to 85/15 or also various ranges within these range limits proved advantageous in initial studies by the inventors.

The performance of the process can advantageously be conducted in that during the molding process—to align the axes of the passage channels at an acute angle to one another toward a common focal point—the mold cores in the molding tool are arranged and designed corresponding to the orientation, the grid and the shape of the passageways, which are kept in a storage unit outside of a wall section of the molding tool and are pulled out of the passageways after the filling and initial solidification of the injection mass and before ejection of the mold.

Additional advantageous measures for performing the process include the fact that to prepare for the molding sequence, the mold cores are placed in the molding position using an adjusting unit that moves the storage unit with the mold cores and after initial solidification, they are drawn out of the passages by means of the adjusting unit that moves the storage unit.

Additional advantages for performing the process arise from the fact that the mold cores are introduced into the wall section of the molding tool through individually allocated passageways and pulled out again through them, in order to compensate for a lateral movement component, at least in the and/or y direction and possibly also in the z direction, caused by skewing of the passageways during insertion and removal.

The beam guiding grid is advantageously constructed such that the passageways with their central axes are aligned at an acute angle with one another based on a common focus point.

Precise formation of the beam guiding grid is furthermore achieved by the fact that the passageways expand conically from a beam incidence side toward a beam exit side, wherein the angle of conicity relative to the central axis is a maximum of 1°.

Additional advantageous embodiments of beam guiding grids consist of the fact that the grid spacing from center to center of the passageways is a maximum of 2 mm and the thickness of the wall areas at their thinnest point is a maximum of 200 µm.

BRIEF DESCRIPTION OF THE DRAWINGS

FIG. 1 a schematic view of the insertion of a beam guiding grid in an X-ray device such as a computed tomograph, FIG. 2 an enlarged sectional view of a beam guiding grid in longitudinal section, FIG. 3 a sectional top view of a beam guiding grid in schematic representation and FIG. 4 an injection molding tool for producing a beam guiding grid in a perspective sectional view in schematic representation.

DETAILED DESCRIPTION OF THE INVENTION

Figure 3:
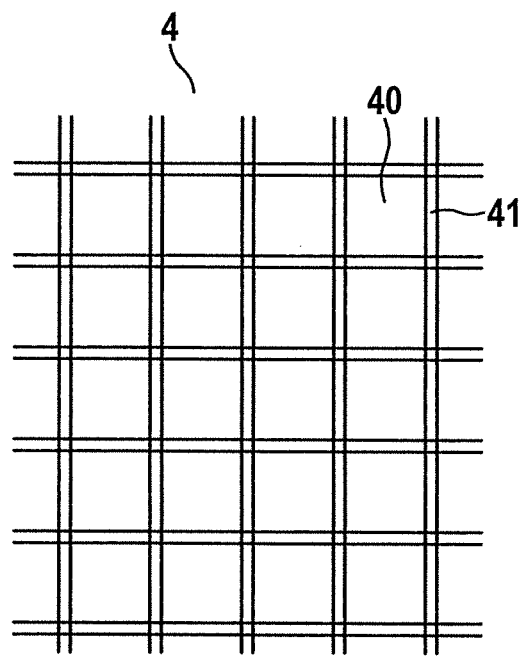

In FIG. 1 the use of a beam guiding grid, also known as an anti-scattering grid or collimator, in an imaging device 1 for X-ray diagnostics is shown. At a focus point, for example at a distance of one meter, a radiation source 2 for emitting X-rays is arranged, which penetrate a body K with an object O to be examined. Then the X-rays, which contain the image information of the object O, pass through passageways 40 of the beam guiding grid 4 as primary rays 30 and are recorded by a receiver unit 5, which generally has receiver elements arranged as a matrix. Then an analyzable image of the object O is reconstructed from the individual recordings. An examination using gamma rays, i.e., with beams from the area of electromagnetic radiation following the shorter wavelength range of the X-rays, can also be performed similarly. Then the radiation source 2 is designed as a gamma radiation source and the receiver unit 5 is selected correspondingly.

As is further shown schematically in FIG. 1, at scattering centers contained, for example, in the body K, scattered radiation 31 may be formed upon passage of the beam 3, interfering with or obscuring the image obtained from the primary rays 30, so that evaluation of the image information is made difficult or can no longer take place in detail. With the beam guiding grid, scattered radiation is largely absorbed because the passageways 40 of the beam guiding grid 4 are surrounded with absorbent wall areas 41. Suitable absorbent materials which contain appropriate metals, for example tungsten or metals with similar X-ray- or gamma-ray-absorbing properties, are known in and of themselves.

So that the primary rays 30 can pass through the beam guiding grid 4 unimpeded, the passageways 40 with their absorbent wall areas are aligned on their focal point located in the radiation source 2, as is indicated in the sectional drawing according to FIG. 2. As is apparent from FIG. 3, the beam guiding grid 4 extends two-dimensionally and, for example is provided with passageways 40 with cross sections of rectangular, square, or polygonal shape; round, oval or other appropriate free-form shape.

The recording device 1 has a system comprising a plurality of adjacently arranged beam guiding grids 4 to obtain the most complete possible image of the object O. For example, the individual beam guiding grids 4 have a height (in reference to the beam passage) of between 4 and 20 mm and a length and width of several centimeters, and the cross-sectional dimension of the passageways is, for example, in the range of about one millimeter, e.g., between 0.5 and 1.5 mm. The thickness of the wall regions is between, e.g., 40 µm and 200 µm, for example between 60 µm and 150 µm, wherein a range between e.g., 80 µm and 120 µm can be suitable. The oblique positioning of the passageways 40 relates, for example, to a common focal point at a distance of one meter, so that the individual passageways 40 travel at an acute angle relative to one another with regard to the focal point.

As was described initially, the requirements on the described design of the beam guiding grid 4 entail a relatively high cost. To make the cost more economical, especially in view of large numbers of pieces and uniformly good workmanship, the beam guiding grids 4 according to the invention are produced using injection molding technology, wherein the design and the procedure are characterized by special measures, as is shown schematically by FIG. 4.

Figure 4:
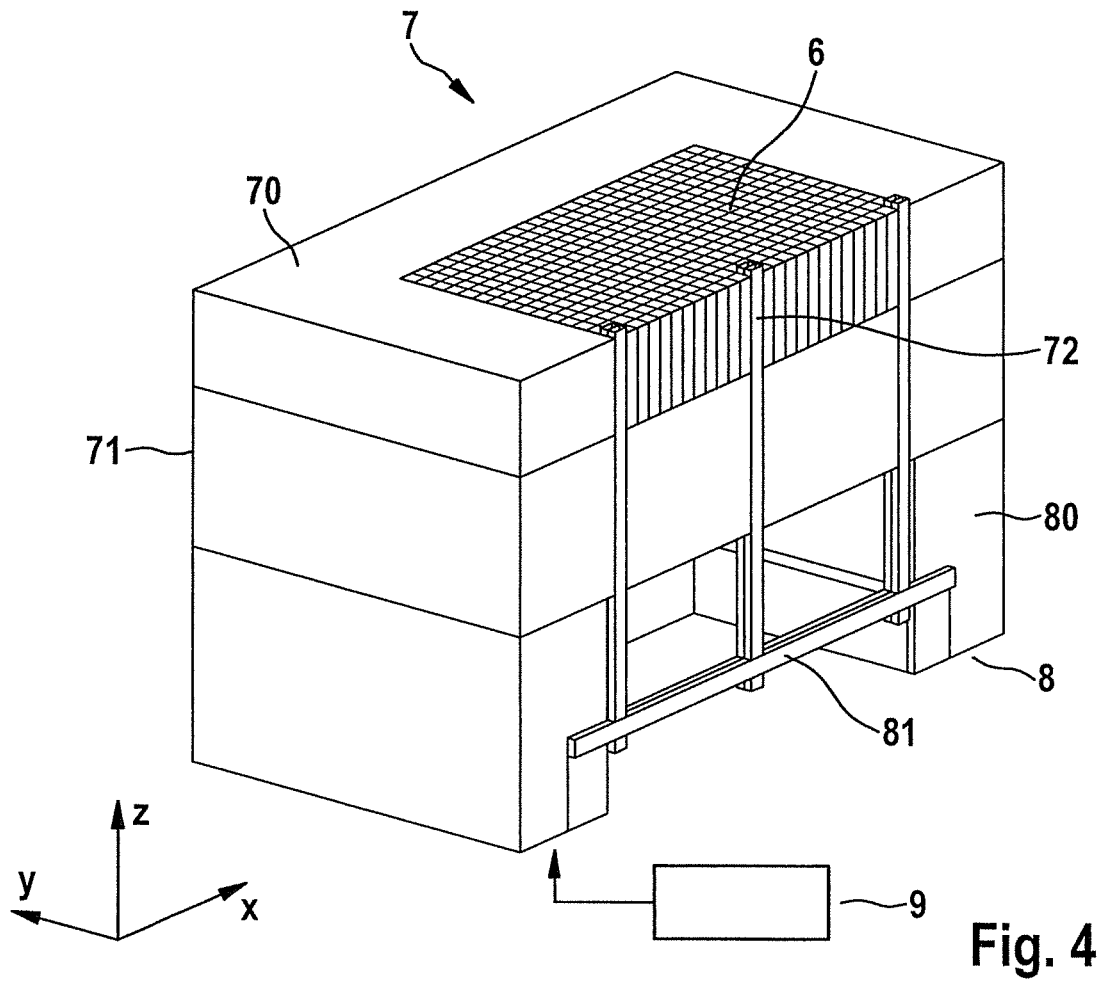

FIG. 4 shows an injection tool disposed in an injection molding machine at the outlet in front of an injection nozzle that injects an injection material. The injection tool has a molding tool 7 with a cavity for an injection body subsequently forming the beam guiding grid 4 or a molding 6. A plate-shaped molding 70 is arranged on the nozzle side and forms the outer peripheral contour of the molding 6. Beneath the molding 70 on the discharge side is an additional plate-shaped molding 71. In the additional molding 71 on the discharge side, passage openings are arranged, through which displaceable mold cores 72 are passed in the direction of the passageways 40 is present in the molding 6. Only a few of these pin-like mold cores 72 are shown in FIG. 4. Actually, such mold cores 72 are present for all of the passageways 40.

Each of the mold cores 72 is individually aligned at the necessary acute angle with reference to the focal point toward a vertical axis (z-axis) of the beam guiding grid 4 and the molding 6, wherein the beam guiding grid 4 and the molding 6 each extend in length and width in a plane perpendicular to in the X/y direction. With mold cores 72 introduced into the cavity, an injection composition is introduced through the corresponding nozzle of the injection molding machine for producing the molding 6 to produce the absorbent wall regions 41, wherein the injection composition is formed from a mixture of radiation-absorbing metal powder and binder, thus especially tungsten powder and binder.

The heated liquid injection composition is then cooled to a temperature that causes pre-solidification of the molding 6. Then the mold cores 72 are withdrawn from the passageways of the molding 6 by means of a holder 80 bearing the mold cores 72 by actuating an adjusting unit 9. For this purpose, the holder 80 has mold core holders 81 which permit lateral displacement with respect to the z direction during the withdrawal of the mold cores 72 from the molding 6, since during the withdrawal of the mold cores 72 in the z direction, because of the oblique positioning of the passageways 40, a lateral motion component in the X or y direction is superimposed on the mold cores 72. The mounting of the mold cores 72 in the mold core holders 81 is therefore of the floating type. Correspondingly, the floating design also makes lateral displacement in the X and y directions possible during the introduction of the mold cores 72 through the passages of the additional mold part 71 on the ejector side.

As FIG. 4 shows, for the floating support, for example, a few horizontal guides extending in the X direction for a respective line of mold cores 72 are present, while the guides with the respective mold cores 72 can in turn be displaced in the y direction, so that in the direction of the opening as well a corresponding alignment of the passageways 40 can be done to compensate during the introduction or removal of the mold cores 72.

As an advantageous measure for unmolding it has been found that the mold cores 72 are conically tapered slightly or more or less extensively in the direction toward the focal point.

The opening of the injection molding tool or molding tool 7 to eject the molding 6 or the beam guiding grid 4 takes place between the molding 70 and the additional molding 71.

It was also found during studies by the inventor that for example a thermoplastic made of polyether ketone, especially polyether ether ketone (PEEK), can be advantageously used as the binder, allowing stable properties and moldability at a relatively high temperature (e.g., between 330° C. and 450° C.). The temperature difference between the temperature during filling of the molding tool 7 and withdrawal of the mold cores 72 is, for example, 70° C., for which the temperature control system of the injection molding machine has been made appropriately controllable. Other thermoplastic binders or duroplastic binders are also conceivable. The degree of filling of the injection compound, homogeneously prepared with metal powder, falls in the range, in parts by volume of metal powder or tungsten powder, from 30/70 to 98/2 parts metal powder to binder, e.g., between 40/60 to 95/5, 50/50 to 90/10 or 60/40 to 85/15, wherein ratios falling between these may also be considered. The materials selected for the radiation-absorbing metal powder and the binder as well as the geometric ratios of the beam guiding grid and thickness of the wall areas must also be considered.

The process according to the invention gives an economical production method for beam guiding grids 4, especially in large quantities and with consistently high quality.

The invention claimed is:

1. A process for producing a beam guiding grid, including a molding, provided with a grid of passageways and wall areas surrounding the passageways, formed by a mixture of radiation-absorbing metal powder and binder, comprising:
producing the molding by injection molding,
wherein a homogenized mixture is filled, as a flowable prepared injection compound, using an injection machine into a molding tool forming the molding, into which movable mold cores were introduced before the injection compound was filled in.

2. The process according to claim 1, wherein the binder used for the injection process is a preheated and plasticized thermoplastic or duroplastic material.

3. The process according to claim 2, wherein a polyether ketone is used as the thermoplastic material.

4. The process according to claim 1, wherein a ratio of metal powder to binder in volume-percent is in a range of 30/70 to 98/2.

5. The process according to claim 1, wherein during the molding, to produce axes of the passageways align at an acute angle to one another toward a common focal point, the mold cores in the molding tool are arranged and shaped according to an orientation, the grid and the shape of the passageways, held outside of a wall section of the molding tool on a storage unit and after introduction and pre-solidification of the injection compound and prior to ejecting the molding, are withdrawn from the passageways.

6. The process according to claim 5, wherein for preparing for the molding process, the mold cores are placed in molding position using a displacement unit that moves the storage unit with the mold cores into molding position and after pre-solidification, are withdrawn from the passageways by the displacement unit that moves the storage unit.

7. The process according to claim 5, wherein the mold cores are introduced through individually assigned feed-throughs in the wall section of the molding tool and drawn through the feed-throughs, wherein mold cores are held in a floating manner on the storage unit to compensate for a lateral movement component in the x and/or y direction due to oblique positioning of the passageways and the feed-throughs during the introduction and withdrawal processes.

8. A beam guiding grid, formed from a molding with a grid of passageways and X-ray or gamma ray absorbing wall areas surrounding them, molded from a homogeneously distributed metal powder bound in a binder, especially tungsten powder, according to claim 1, wherein the binder is a thermoplastic or duroplastic plastic or predominantly contains such a plastic.

9. The beam guiding grid according to claim 4, wherein the passageways are aligned toward a focal point with their central axes at an acute angle with respect to one another.

10. The beam guiding grid according to claim 9, wherein the passageways taper conically from a beam incidence side to a beam exit side, wherein the angle of conicity with respect to the central axis is a maximum of 1°.

11. The beam guiding grid according to claim 8, wherein the grid distance from center to center of the passageways is a maximum of 2 mm and the thickness of the wall regions at their thinnest point is a maximum of 200 μm.

12. An arrangement of a plurality of beam guiding grids structured according to claim 8, in an optical system containing at least one X-ray source, in which the passageways are aligned with their central axes toward the X-ray source.

* * * * *